United States Patent [19]

Kao

[11] Patent Number: 5,194,447
[45] Date of Patent: Mar. 16, 1993

[54] SULFONYLCARBAMATES OF RAPAMYCIN

[75] Inventor: Wenling Kao, Chester, Pa.

[73] Assignee: American Home Products Corporation, New York, N.Y.

[21] Appl. No.: 837,048

[22] Filed: Feb. 18, 1992

[51] Int. Cl.$^5$ ............... C07D 491/16; A61K 31/395; A61K 31/685; C07F 7/04
[52] U.S. Cl. .................... 514/542; 514/546
[58] Field of Search .................. 540/452, 456

[56] References Cited

U.S. PATENT DOCUMENTS

| | | | |
|---|---|---|---|
| 3,992,992 | 12/1975 | Sehgal et al. | 424/192 |
| 3,993,749 | 11/1976 | Sehgal et al. | 424/122 |
| 4,316,885 | 2/1982 | Rakhit | 424/122 |
| 4,401,653 | 8/1983 | Eng | 424/124 |
| 4,650,803 | 3/1987 | Stella et al. | 514/291 |
| 4,885,171 | 12/1989 | Sehgal et al. | 424/122 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,889 | 3/1992 | Calne | 514/291 |

OTHER PUBLICATIONS

U.S. Ser. No. 07/686,727 filed Apr. 17, 1991-Kao, Vogel, Musser.
Vezina, C. J. Antibiot. 28, 721-726 (1975).
Sehgal, S. N., J. Antibiot. 28, 727-732 (1975).
Baker, H., J. Antibiot. 31, 539-545 (1978).
Martel, C., Can. J. Physiol. Pharmacol. 55, 48 (1977).
Staruch et al., FASEB 3, 3411 (1989).
Dumont, F, FASEB 3,5256(1989).
Calne et al., Lancet, 1183-1185 (1978).
Morris, R. Med. Sci. Res. 17:877 (1989).

Primary Examiner—Robert T. Bond
Attorney, Agent, or Firm—Arnold S. Milowsky

[57] ABSTRACT

A compound of the structure

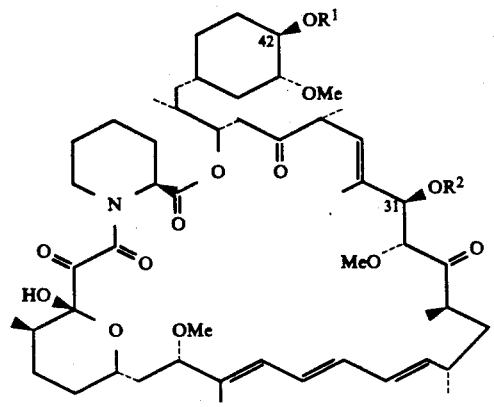

wherein
$R^1$ and $R^2$ are each, independently, hydrogen or —CONHSO$_2$-Ar; and
Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di, or tri-substituted; with the provision that $R^1$ and $R^2$ are not hydrogen; or or a pharmaceutically acceptable salt thereof which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections.

7 Claims, No Drawings

SULFONYLCARBAMATES OF RAPAMYCIN

BACKGROUND OF THE INVENTION

This invention relates to carbamates of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and European Patent Application 0401747 A2].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, antifungal, and antitumor agents having the structure

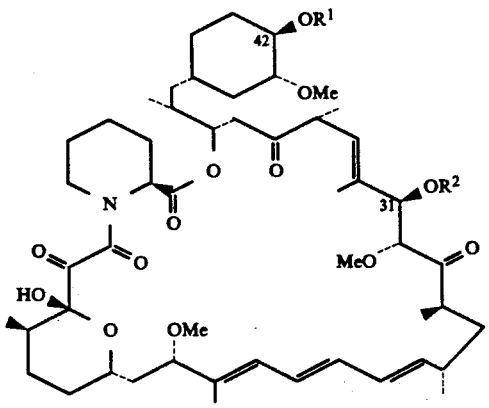

wherein
$R^1$ and $R^2$ are each, independently, hydrogen or $-CONHSO_2-Ar$; and
Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, $-SO_3H$, $-PO_3H$, and $-CO_2H$;
with the proviso that $R^1$ and $R^2$ are not both hydrogen; or a pharmaceutically acceptable salt thereof when the Ar group contains a basic nitrogen or when the Ar group is substituted by dialkylamino of 1-6 carbon atoms per alkyl group, $-SO_3H$, $-PO_3H$, or $-CO_2H$.

The pharmaceutically acceptable salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic hydrochloric, hydrobromic, phosphoric, nitric, sulfuric, methanesulfonic, and similarly known acceptable acids and.

Of these compounds, preferred members are those in which Ar is optionally mono-, di-, or tri- substituted phenyl. When Ar is substituted with arylalkyl of 7-10 carbon atoms, it is preferred that aryl portion of the arylalkyl moiety be a phenyl group.

The compounds of this invention carbamylated at the 42-position or at both the 31- and 42-positions can be prepared by reacting rapamycin with an isocyanate having the general structure $$O=C=N-SO_2-Ar$$

under neutral conditions or in the presence of a base, such as pyridine.

The 31-carbamylated compounds of this invention can be prepared by protecting the 42-alcohol of rapamycin with a protecting group, such as with a tert-butyl dimethylsilyl group, followed by carbamylation of the 31-position with an isocyanate with the general structure shown above. Removal of the protecting group provides the 31-carbamylated compounds. In the case of the tert-butyl dimethylsilyl protecting group, deprotection can be accomplished under mildly acidic conditions.

Having the 31-position carbamylated and the 42-position deprotected, the 42-position can be reacted with a different isocyanate than was reacted with the 31-alcohol, to give compounds having different carbamates at the 31- and 42-positions. Alternatively, the 42-carbamylated compounds, prepared as described above, can be reacted with a different isocyanate to provide compounds having different carbamates at the 31- and 42-positions.

The isocyanates used to prepare the compounds of the invention are commercially available or can be prepared by methods that are disclosed in the literature. March [*Advanced Organic Chemistry*, 3d ed., pp. 391, 452, and 479 (1985)] describes a general method for preparing arylsulfonyl isocyanates, that can be used where the arylsulfonylisocyanate is not commercially available. The following scheme is illustrative of one method starting from an aryl moiety. Other methods of preparing arylsulfonyl isocyanates are known in the literature.

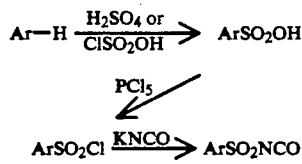

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft. The ability to prevent or treat transplantation rejection was also demonstrated in an in vivo heart allograft standard test procedure.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentration of rapamycin, cyclosporin A, or test compound. Cells are harvested and incorporated radioactivity is determined. Inhibition of lymphoproliferation is assessed as percent change in counts per minute from non-drug treated controls. The results are expressed according to the following ratio.

$$\frac{^3H\text{-control thymus cells} - H^3\text{-rapamycin-treated thymus cells}}{^3H\text{-control thymus cells} - H^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3H\text{-}PLN \text{ cells control } C3H \text{ mouse} - {}^3H\text{-}PLN \text{ cells rapamycin-treated } C3H \text{ mouse}}{^3H\text{-}PLN \text{ cells control } C3H \text{ mouse} - {}^3H\text{-}PLN \text{ cells test compound-treated } C3H \text{ mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385-402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1

| Compound | LAF (ratio) | PLN (ratio) | Skin Graft (days ± SD) |
|---|---|---|---|
| Example 1 | 0.91 | 0.84 (p.o.) 1.03 (i.p.) | 11.2 ± 0.4 |
| Example 3 | 0.74 | 0.47 | + |
| Example 4 | 0.10 | + | + |
| Rapamycin | 1.00 | 1.00 | 12.0 ± 1.7 |

+ Not evaluated.

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6-7 days without the use of an immunosuppressive agent, the increased survival time of the skin graft when treated with the compounds of this invention further demonstrates their utility as immunosuppressive agents.

The ability of the compounds of this invention to prevent or treat transplantation was demonstrated in a heterotropic heart allograft standard pharmacological test procedure that emulates transplantation rejection that occurs in humans. The following briefly describes the procedure that was used. Male BN rat neonate donors (less than 5 days of age) were humanely sacrificed, the thymus was dissected away from the heart. All connections with the thoracic cavity were severed and the heart was removed from the chest cavity and placed in cooled RPMI media where all adherent fat and fascia were removed. The heart was bisected in half, along the midline from the apex to the root of the aorta, to generate two approximately equal halves each containing atrial and ventricular tissue. Recipient male Lewis rats were anesthetized with phenobarbitol (50 mg/mL; i.p.), the left inner ear was swabbed with povidine iodine, and 1 mL RPMI was injected subcutaneously above the cartiledge plate to produce a fluid filled sac. A stab incision was made to the sac, into which was inserted a single half heart fragment. The pocket was sealed with a single drop of Vet-Seal (3M Animal Care Products). Recipients were divided into treatment groups of 10 rats each and the compounds to be evaluated were administered at a dosage of 225 µg/day following the transplantation procedure until graft failure occurred. Administration was i.p., either by manual injection or via an Azlet osmotic pump that was implanted into the peritoneum of the recipient rat. Grafts were inspected for loss of cardiac activity on day 7 post-transplant and subsequently on alternate days. Graft survival time is defined as the post-transplant day on which the heart graft has lost all contractile activity by visual inspection and/or cardiac monitor. Individual rejection times were averaged to produce a mean survival time for each treated group. The following table shows the results obtained for a representative compound of this invention. The control group represents rats that received the allograft and no test compound. Rapamycin was evaluated for the purpose of comparison.

TABLE 2

| Treatment Group | Mean Survival Time (days) |
|---|---|
| Control | 11.5 |
| Example 1 | 34.4 |
| Rapamycin | 38 |

As shown in Table 2, treatment with a representative compound of this invention significantly ($p<0.05$) prolonged survival time of the transplanted allograft. The untreated allograft was rejected by 11.5 days, whereas treatment with a representative compound of this invention prevented rejection until 34.4 days. As such, the results of this standard pharmacological test procedure demonstrate that the compounds of this invention are useful in preventing or treating transplantation rejection.

Because the compounds of this invention are structurally similar to rapamycin and have a similar activity profile to rapamycin, the compounds of this invention also are considered to have antitumor and antifungal activities.

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease, and eye uveitis; solid tumors; and fungal infections.

As the compound of Example 3 was prepared via its 42-silylated intermediate (Example 2), the compound of Example 2 is therefore a useful as an intermediate of compounds of this invention.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1–5 percent, preferably 2%, of active compound which may be administered to a fungally affected area.

The following examples illustrate the preparation of representative compounds of this invention.

EXAMPLE 1

Rapamycin 42-ester with phenylsulfonylcarbamic acid

A solution of 192 mg of rapamycin in 1 mL toluene was treated at 0° under nitrogen with 37 mg of benzenesulfonyl isocyanate in 1 mL toluene. After stirring at 0° under nitrogen for one hour, the reaction mixture was diluted with 100 ml of ethyl acetate and washed with brine (3×20 ml). The ethyl acetate solution was dried with magnesium sulfate and evaporated. The residue was chromatographed on silica gel. Elution with ethyl acetate/hexane (1:1) afforded 36 mg of the title compound as a white foam.

IR (KBr) 3440 (OH), 2910, 1735 & 1710 (C=O), 1635 (aromatic), 1440, 1160, 1080 and 980 cm$^{-1}$. NMR (CDCl$_3$, 400 MHz): δ 8.04 (m, 2H, aromatic), 7.65 (m, 1H, aromatic), 7.56 (m, 2H, aromatic), 3.41 (s, 3H, OCH$_3$), 3.34 (s, 3H, OCH$_3$), 3.13 (s, 3H, OCH$_3$). MS (neg. ion FAB): 1095 (M−), 590. 321.

EXAMPLE 2

Rapamycin 42-tertbutyldimethylsilyl ether-31-ester with phenyl sulfonyl carbamic acid Rapamycin (0.914 g) was added to a solution of 0.204 g imidazole and 0.165 g tert-butyldimethylsilyl chloride in 4 mL dimethylformamide at 0° and stirred under nitrogen for 16 hours at 20°. Brine (100 mL) was added, the product was extracted into ether, washed with brine, dried over MgSO$_4$ and evaporated. Chromatography on silica gel afforded 0.65 g of rapamycin-42-tert-butyldimethylsilyl ether as a white solid.

A solution of 308 mg of rapamycin-42-tert-butyldimethylsilyl ether in 1 mL toluene was treated at 0° under nitrogen with 109 mg of benezenesulfonyl isocyanate in 1 mL toluene. After stirring at 0° under nitrogen for three hours, the reaction mixture was diluted with 100 mL ethyl acetate and washed with brine 2×20 ml). The ethyl acetate solution was dried with magnesium sulfate and evaporated. The residue was chromatographed on silica gel. Elution with ethyl acetate/hexane (1:1) afforded 310 mg of the title compound as a white foam.

IR (KBr): 3400 and 3240 (OH), 2915, 1740 and 1710 (C=O), 1640, 1440, 1160, 1080 cm$^{-1}$. NMR (CDCl$_3$, 400 MHz): δ 8.00 (m, 2H, aromatic), 7.55 (m, 3H, aromatic), 3.45 (s, 3H, OCH$_3$), 3.27 (s, 3H, OCH3), 3.13 (s, 3H, OCH$_3$). MS (neg. ion FAB): 1209 (M−), 590, 156.

EXAMPLE 3

Rapamycin-31-ester with phenylsulfonylcarbamic acid

A solution of 250 mg of Rapamycin-42-tert-butyldimethylsilyl ether-31-ester with phenylsulfonylcarbamic acid in 2 mL of tetrahydrofuran was treated with 2 mL water and 6 mL acetic acid. After stirring at room temperature under nitrogen for 20 hours, the mixture was diluted with 130 mL ethyl acetate and washed with brine (2×20 ml). The ethyl acetate solution was dried with magnesium sulfate and evaporated to dryness to give 208 mg of the title compound as a white foam.

IR (KBr): 3400 (OH), 2930, 1730 (C=O), 1640 (aromatic), 1440, 1340, 1160, 1085 cm$^{-1}$. NMR (CDCl$_3$, 400 MHz): δ 8.0 (m, 2H, aromatic), 7.59 (m, 3H, aromatic), 3.41 (s, 3H, OCH$_3$), 3.26 (s, 3H, OCH$_3$). MS (neg. ion FAB): 1095 (M−), 589, 321.

EXAMPLE 4

Rapamycin 42-ester with (4-chlorophenylsulfonyl)carbamic acid

A solution of 400 mg of rapamycin in 10 mL ether/toluene (1:4) was treated at −10° under nitrogen with 100 mg of 4-chlorobenzenesulfonyl isocyanate in 1 mL toluene. The mixture was stirred at 0° under nitrogen for 3.5 hours, diluted with 120 mL of ethyl acetate, washed with saturated sodium bicarbonate solution, followed by a water wash, and dried with magnesium sulfate. The ethyl acetate solution was evaporated and the residue chromatographed on silica gel. Elution with ethyl acetate afforded 100 mg of the title compound as a white solid, mp 142°-146°. The title compound was isolated as a trihydrate.

$^1$H NMR (CDCl$_3$, 400 MHz), δ 8.0 (d, J=13 cps, 2H, aromatic protons meta to sulfonyl group), 7.53 (d, J=13 cps, 2H, aromatic protons ortho to sulfonyl group), 3.30 (s, 3H, OCH$_3$), 3.20 (s, 3H, OCH$_3$), 3.13 (s, 3H, OCH$_3$) ppm. MS (neg ion FAB): 1129 (MH-). IR KBr max 3430 (OH), 2930, 1740, 1730 (both C=O), 1640 (amide C=O), 1450, 1350 (—SO$_2$—), 1160 (—SO$_2$—), 1160 (—SO2—), 1090, 985 cm$^{-1}$.

Anal. Calcd. for C$_{58}$H$_{83}$ClN$_2$O$_{16}$S.3 H$_2$O: C 58.74; H 7.56; N 2.35 Found: C 58.92; H 7.99; N 2.17

EXAMPLE 5

Rapamycin 42-ester with (3-methylphenylsulfonyl) carbamic acid

A solution of 400 mg rapamycin in 10 mL ethyl acetate/ether (¼) was treated at −10° under nitrogen with 127 mg of 3-methylphenylsulfonyl isocyanate in 2 mL ether. THe mixture was stirred at 0° under nitrogen for 4.5 hours, diluted with 120 mL ethyl acetate, washed with a saturated sodium bicarbonate solution, and dried with magnesium sulfate. The ethyl acetate solution was evaporated and the residue chromatographed on silica gel. Elution with ethyl acetate/n-hexane (1:1) afforded 270 mg of the title compound as a white powder, mp 116°-120°.

$^1$H NMR (CDCl$_3$, 400 MHz) δ 8.13 (d, J=13 cps, 1H, aromatic proton ortho to sulfonyl group), 7.53 (m, 1H, aromatic proton, para to sulfonyl group), 7.39 (m, 1H, aromatic protons para to methyl group), 7.33 (d, J=13 cps, 1H, aromatic ortho to methyl group), 3.23 (s, 3H, OCH$_3$), 3.18 (s, 3H, OCH3), 3.14 (s, 3H, OCH$_3$), 2.67 (s, 3H, aromatic methyl) ppm. MS (neg. ion FAB): 1109 (MH- ). IR KBr max 3450 (OH), 2940, 1740, 1720 (C=O), 1640 (amide C=O), 1450, 1340 (—SO$_2$—), 1160 (—SO$_2$—), 990 cm$^{-1}$.

EXAMPLE 6

Rapamycin 31,42-diester with phenylsulfonylcarbamic acid

A solution of 200 mg of rapamycin 42-ester with phenylsulfonylcarbamic acid in 3 mL ethyl acetate/ether (1:1) was treated at 0° under nitrogen with 200 mg of benzenesulfonyl isocyanate in 0.5 mL of ether. After stirring at 0° under N₂ for 18 hours and at 22° under N₂ for 3 hours, the reaction mixture was diluted with 120 mL ethyl acetate, washed with a saturated sodium bicarbonate solution, and then washed with brine. The ethyl acetate solution was dried with magnesium sulfate and evaporate. The residue was chromatographed on silica gel. Elution with ethyl acetate afforded 75 mg of the title compound as a white foam, mp 104°–108°.

NMR (CDCl₃, 400 MHz): δ 8.03 (m, 2H, aromatic), 7.55 (m, 3H, aromatic), 3.26 (s, 3H, OCH₃), 3.22 (s, 3H, OCH₃), 3.13 (s, 3H, OCH₃) ppm. MS (neg. ion FAB): 1278 (MH⁻). IR (KBr): 3340 (OH), 2930, 1730 & 1715 (C=O), 1630 (aromatic), 1445, 1290, 1160, 1095, 990 cm−1.

What is claimed is:

1. A compound of the formula

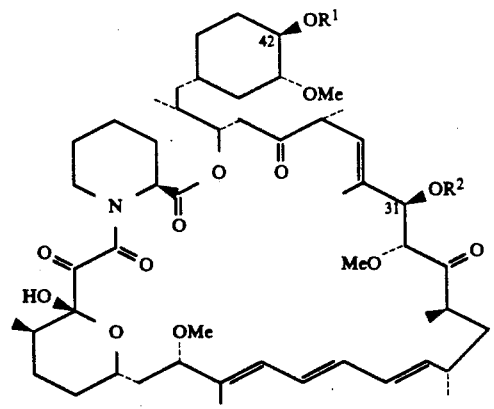

wherein
R¹ and R² are each, independently, hydrogen or —CONHSO₂-Ar; and Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1-6 carbon atoms, phenylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;
with the proviso that R¹ and R² are not both hydrogen; or a pharmaceutically acceptable salt thereof when the Ar group contains a basic nitrogen or when the Ar group is substituted by dialklyamino of 1-6 carbon atoms per alkyl group, —SO₃H, —PO₃H, or —CO₂H.

2. A compound of claim 1 wherein Ar is phenyl; the phenyl group being optionally mono-, di-, or tri-substituted or a pharmaceutically acceptable salt thereof.

3. A compound of claim 1 which is rapamycin 42-ester with phenylsulfonylcarbamic acid.

4. A compound of claim 1 which is rapamycin-31-ester with phenylsulfonylcarbamic acid.

5. A compound of claim 1 which is rapamycin 42-ester with (4-chlorophenylsulfonyl)carbamic acid.

6. A compound of claim 1 which is rapamycin 42-ester with (3-methylphenylsulfonyl) carbamic acid.

7. A compound which is rapamycin 42-tertbutyldimethylsilyl ether-31-ester with phenylsulfonylcarbamic acid.

* * * * *